United States Patent
Tankovich

[11] Patent Number: 5,925,035
[45] Date of Patent: *Jul. 20, 1999

[54] HAIR REMOVAL METHOD

[75] Inventor: Nikolai I. Tankovich, San Diego, Calif.

[73] Assignee: ThermoLase Corporation, San Diego, Calif.

[*] Notice: This patent is subject to a terminal disclaimer.

[21] Appl. No.: 08/695,200

[22] Filed: Aug. 1, 1996

Related U.S. Application Data

[63] Continuation of application No. 08/280,928, Jul. 26, 1994, abandoned, which is a continuation-in-part of application No. 08/257,021, Jun. 8, 1994, Pat. No. 5,423,803, which is a continuation-in-part of application No. 08/005,810, Jan. 19, 1993, Pat. No. 5,425,728, which is a continuation-in-part of application No. 07/783,789, Oct. 29, 1991, Pat. No. 5,226,907.

[51] Int. Cl.$^6$ .......................... A61B 17/36; A61B 17/50
[52] U.S. Cl. .................................. 606/9; 606/133; 606/2
[58] Field of Search .................................. 606/1, 9, 131, 606/133; 128/898

[56] References Cited

U.S. PATENT DOCUMENTS

| | | |
|---|---|---|
| 3,495,962 | 2/1970 | Norton et al. . |
| 3,538,919 | 11/1970 | Mayer . |
| 3,693,623 | 9/1972 | Harte et al. . |
| 3,769,963 | 11/1973 | Goldman et al. . |
| 3,794,028 | 2/1974 | Mueller et al. . |
| 3,834,391 | 9/1974 | Block . |
| 3,900,034 | 8/1975 | Katz et al. . |
| 4,336,809 | 6/1982 | Clark . |
| 4,388,924 | 6/1983 | Weissman et al. . |
| 4,434,064 | 2/1984 | Chao et al. . |
| 4,461,294 | 7/1984 | Baron . |
| 4,608,978 | 9/1986 | Rohr . |

(List continued on next page.)

FOREIGN PATENT DOCUMENTS

| | | |
|---|---|---|
| 1041610 | 6/1974 | Canada . |
| 1208702 | 7/1986 | Canada . |
| 64967A2 | 4/1995 | European Pat. Off. . |
| 2267122 | 4/1975 | France . |
| 2595239 | 6/1982 | France . |
| 2590791 | 6/1987 | France . |
| 2515697 | of 0000 | Germany . |
| 32209G2 | 6/1982 | Germany . |

(List continued on next page.)

OTHER PUBLICATIONS

Finkelstein et al., "Epilation of Hair–Bearing Urethral Grafts Utilizing the Neodymium: YAG Surgical Laser", 1990, Lasers in Surgery and Medicine, vol. 10, No. 2, New York.
Porphyrins in Tumor Phototherapy—Andereoni 1984—pp. 143–155.
Investigation and Therapy in Dermatology A. Anders, et al—Conf. Laser 77 Optics—Electronics (20–24 Jun. 1977).

*Primary Examiner*—Glenn K. Dawson
*Attorney, Agent, or Firm*—Fish & Richardson P.C.

[57] ABSTRACT

A process for the permanent destruction of unwanted human hair. Hair duct in a section of skin in which the unwanted hair is growing is contaminated with a contaminant having a very large number of small particles having a high absorption at at least one frequency band of light. The skin section is then illuminated with a series of short pulses of light at the frequency band of high absorption, the first of the short pulses having sufficient energy to cause a large number of the particles to explode into two or more fragments so as to spread said contaminant in the hair ducts and subsequent pulses having sufficient energy to cause a large number of the fragments to further explode into additional fragments to further spread the contaminant in the hair duct. The explosions and energy is transferred to and from the particles and fragments causing damage to skin tissue surrounding said hair ducts so as to cause death to the hairs growing in the ducts. In a preferred embodiment the particles are 1 micron graphite particles and each section is illuminated with about 5 laser pulses at 1.06 micron wavelength produced by a Nd:YAG laser, each pulse having an energy density of about 3 Joules/cm$^2$ and a pulse width of about 10 nano seconds.

26 Claims, 7 Drawing Sheets

U.S. PATENT DOCUMENTS

| | | |
|---|---|---|
| 4,617,926 | 10/1986 | Sutton . |
| 4,712,543 | 12/1987 | Baron . |
| 4,813,412 | 3/1989 | Yamazaki . |
| 5,059,192 | 10/1991 | Zaias . |
| 5,423,803 | 6/1995 | Tankovich et al. .................. 606/131 |
| 5,752,948 | 5/1998 | Tankovich et al. .................. 606/133 |
| 5,752,949 | 5/1998 | Tankovich et al. .................. 606/133 |

FOREIGN PATENT DOCUMENTS

| | | |
|---|---|---|
| 63-249577 | 10/1988 | Japan . |
| 1 288 805 | 9/1969 | United Kingdom . |
| 8002640 | 12/1980 | WIPO . |
| WO 85/05021 | 11/1985 | WIPO . |
| 8602783 | 5/1986 | WIPO . |
| WO90/11797 | 10/1990 | WIPO . |
| WO 91/04073 | 4/1991 | WIPO . |
| WO 91/11966 | 8/1991 | WIPO . |
| WO91/13652 | 9/1991 | WIPO . |
| WO91/13653 | 9/1991 | WIPO . |
| WO93/21842 | 11/1993 | WIPO . |
| WO93/21992 | 11/1993 | WIPO . |
| WO 94/08655 | 4/1994 | WIPO . |

HAIR REMOVAL METHOD

This application is a continuation of Ser. No. 08/280,928, filed on Jul. 26, 1994, abandoned, which is a continuation in part of Ser. No. 08/257,021 filed Jun. 8, 1994, now U.S. Pat. No. 5,423,803, which was a CIP of my earlier filed application Ser. No. 08/005,810 filed Jan. 19, 1993 now U.S. Pat. No. 5,425,728, which was a CIP of Ser. No. 07/783,789 filed Oct. 29, 1991 now U.S. Pat. No. 5,226,907 issued Jul. 13, 1993. This invention relates to devices and methods for hair removal and in particular to the use of laser devices for hair removal.

BACKGROUND OF THE INVENTION

The principal methods presently used for hair removal involve the use of electrolysis techniques. These techniques involve some pain, are time consuming, and demand a fair degree of expertise in their application and normally do not guarantee a permanent effect.

Laser use in medicine is well known. For example, lasers are used in surgery for both cutting and cauterization. Lasers have been used for many years for removing tattoos under the surface of the skin. In this case a laser beam penetrates the skin and is absorbed by and destroys the ink particle. A similar procedure has been used for years to remove birth marks where the laser is matched to an absorption peak of the erythrocyte's hemoglobin in the tiny capillaries under the skin to destroy the capillaries.

The prior art of hair removal also includes attempts at removing hair with laser beams. Three such techniques are described in the following United States patents: Weissman et. al., Method for Laser Depilation Device and Method, U.S. Pat. No. 4,388,924; Sutton, Depilation Device and Method, U.S. Pat. No. 4,617,926; and Mayer, Depilation by Means of Laser Energy, U.S. Pat. No. 3,538,919. All of these devices and methods teach the removal of hairs one hair at a time with a narrowly focused laser beam. Therefore, they are relatively inefficient and time consuming. A recent patent by Zaias, U.S. Pat. No. 5,059,192 issued Oct. 22, 1991 discloses a process for using a laser beam matched to the melanin found at the base of the hair follicle and papilla.

It has been known for at least 20 years in the medical profession that selective absorption of laser radiation can sometimes be enhanced by the technique of staining pathological tissues with various vital dyes. (See Goldman U.S. Pat. No. 3,769,963).

In the graphite form of elementary carbon, each carbon atom has three near neighbors and a forth neighbor at a considerably greater distance away, the two lengths being 1.42 A and 3.42 A, respectively. (10,000 angstrom equal 1 micron.) The network of the three nearest neighbors is planar and extends in the two directions of the plane to the boundaries of the solid. The binding forces between the planes are weak and the planes can slip past each other very readily. For this reason, graphite can be used as a lubricating material. Thin layers of graphite can be removed by abrasion and this property is exploited in the ordinary lead pencil in which motion of the graphite rod over paper causes thin layers of the solid to be rubbed off and spread on the paper. For many years laser workers have used paper thinly coated with small particles of graphite to examine the cross section power of certain laser beams. The energy of many laser beams is readily absorbed by the carbon particles and many of the particles react violently exploding off the paper and leaving "footprints" on the paper representative of the cross sectional power distribution of the laser beam.

What is needed is an improved hair removal process that will provide solutions to the above described problems.

SUMMARY OF THE INVENTION

The present invention provides a process for the permanent destruction of unwanted human hair. Hair ducts in a section of skin in which the unwanted hair are growing is contaminated with a contaminant comprised of a very large number of small particles having a high absorption at at least one frequency band of light. The skin section is then illuminated with a series of short pulses of light at the frequency band of high absorption, the first of said short pulses having sufficient energy to cause a large number of the particles to explode into two or more fragments so as to spread said contaminant in said hair ducts and subsequent pulses having sufficient energy to cause a large number of the fragments to further explode into additional fragments to further spread the contaminant in the hair duct. The explosions and energy transferred to and from said particles and fragments causes damage to skin tissue surrounding said hair ducts so as to cause death to the hairs growing in the ducts. In a preferred embodiment the particles are 1 micron graphite particles and each section is illuminated with about 5 laser pulses at 1.06 micron wavelength produced by a Nd:YAG laser, each pulse having an energy density of about 3 Joules/cm$^2$ and a pulse width of about 10 nano seconds.

DETAILED DESCRIPTION OF PREFERRED EMBODIMENTS

Slower Heating of Carbon

U.S. Pat. No. 5,226,907 issued on Jul. 13, 1993 to Applicant discloses a hair removal process in which hair ducts in human skin are contaminated with a carbon-oil suspension. In the disclosed process the suspension is rubbed on the skin so that a portion of the suspension infiltrates into the hair ducts. In that process the surface of the skin is then cleaned leaving the hair ducts contaminated with the carbon-oil suspension. The skin section is then illuminated with a pulsed laser beam which heated the suspension to temperatures of greater than 70–80° C. which destroys tissue adjacent to the carbon-oil suspension. The destruction of this tissue which nourished the hair in the duct causes the hair to die.

The process disclosed in this existing patent of mine works well; however, some problems have been experienced with it. One difficulty we experienced was that even with much massaging and even using ultra-sound devices we were often not able to cause the suspension to infiltrate deeply into the hair duct. The result is that the only destruction of skin tissue was that near the upper part of the duct. Tissue near the bottom of the duct continued to feed the hair and therefore the hair in some of these cases did not die. Another problem with the disclosed procedure was that it was difficult for the doctor to know exactly which areas of the skin had been treated and which had not. Therefore, some sections received more illumination than necessary and some received either none or less than that which was needed for a successful treatment.

Laser Reaction with Carbon

An extremely important aspect of this invention is the reaction of carbon particles to exposure to very short high energy pulses of laser radiation. This reaction is depicted in FIGS. 1A through 1I. These figures depict a one micron particle held in place with transparent tape between two microscope slices and irradiated with a Nd:YAG laser beam.

Figure 1A:
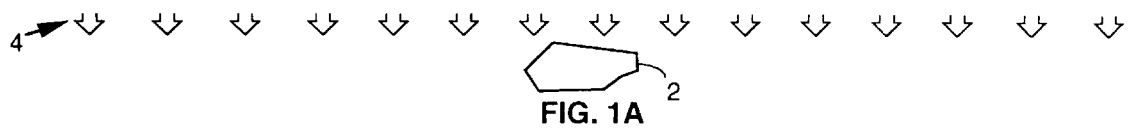
FIGS. 1A through 1I shows how graphite particles are fragmented under certain short pulse laser illumination.

In FIG. 1A a 1 micron particle is depicted being illuminated with a single laser pulse. The pulse is assumed to be produced with a Nd:YAG laser. The energy in each pulse is about 1.5 Joules. The cross sectional area of the pulse beam is 0.5 $cm^2$ so that the fluence (energy density) of the pulse is about 3 $J/cm^2$. The pulse is very short. The temporal width of the pulse at one-half maximum power is about 10 nanoseconds so that the peak power (pulse energy/pulse width) is about 150 megawatts. (By comparison the power output of a large nuclear power plant is about 1,000 megawatts but this is continuous.) The absorption coefficient of carbon for 1.06 micron Nd:YAG laser beam is very large. Essentially all of the beam is absorbed in a 10 micron layer of graphite. If we assume for a qualitative example a graphite cube 1 micron on each side, the energy illuminating the cube would be $3\times10^{-8}$ J. We assume that about 20 percent of the beam is absorbed in the first 1 micron. Therefore we estimate that the 1 micron particles absorbs about $0.6\times10^{-8}$ J. The volume of the cube is $1\times10^{-12}$ $cm^3$, the density of graphite is about 2 $gm/cm^3$ and the specific heat of graphite is 0.507 J/gm C. Therefore, the heat required to heat the particle from 25° C. to the sublimation temperature of graphite, about 3,652 C is about $0.37\times10^{-8}$ J. The heat of formation of carbon vapor from graphite at 25° C. is about $6\times10^4$ J/gm; therefore, the energy needed to vaporize all of the 1 micron particle is about $12\times10^{-8}$ J. Thus, the approximate $0.6\times10^{-8}$ J absorbed is almost twice that needed to heat the particle to its vaporization point, but the energy absorbed is only about 5 percent of the energy needed to vaporize it.

Figure 1B:
Figure 1C:
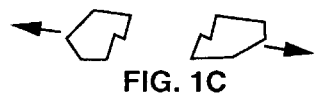

We have discovered that with these very short pulses of about 10 ns the particles are not merely heated but much of the energy of the pulse goes into fracturing violently the particles into two or more fragments. We suspect that the graphite crystal is heated to over 3000° C. and then easily fractured along its weak planes with these short high energy pulses. We believe we have very little evaporation. Our tests prove the violent fracturing. Subsequent pulses continue to have the same impact on the smaller fragment particles. Thus, FIG. 1A shows a one micron particle 2 about to be illuminated with a 10 ns 3 $J/cm^2$ fluence of 1.06 micron laser pulse 4. In FIG. 1B a portion of the pulse is absorbed in particle 2 causing it to fracture violently as shown in FIG. 1C. The two particles have sufficient energy to travel several microns through the sticky substance of the transparent tape before coming to rest at a new location in the sticky substance of the tape.

Figure 1D:
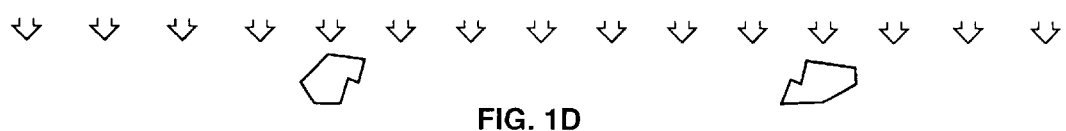
Figure 1E:
Figure 1F:
Figure 1G:
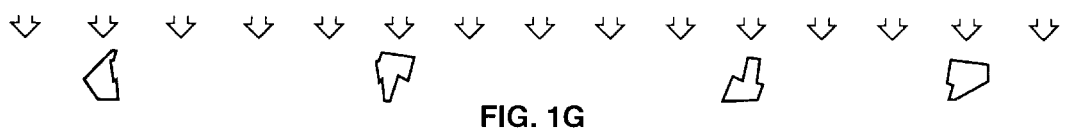
Figure 1H:
Figure 1I:

We assume that the beam is a 10 Hz beam so 0.1 second later another pulse like the first one is coming along as shown in FIG. 1D and as shown in FIG. 1E a portion of the pulse is absorbed in both halves of the original particle causing them to fracture violently as shown in FIG. 1F. The process repeats as shown in FIGS. 1G through 1I representing the 3rd pulse. For at least several of the subsequent pulses, we believe that all of the fragments of the original 1 micron particle will absorb on each pulse about the same amount of energy as was absorbed by the original particle After 5 pulses (assuming a 2 for 1 split in each case) our initial one micron particles would have split into 32 particles and the original particles and all of its daughter particles would have absorbed a total quantity of energy from the beam of about $6\times6\times10^{-8}$ J or $36\times10^{-8}$ J. Most of this energy is very quickly dissipated in the form of heat increasing the temperature of the tissue surrounding the hair duct.

Experiment With Small Particles

In order to confirm the above description I have conducted experiments in which these small carbon particles are irradiated with pulses of the type described above.

When a small number of one micron size particles are placed in an enclosed glass vial in an air atmosphere and irradiated with pulses as described above. The particles are continuously broken into smaller and smaller particles and after about 10–15 pulses they vanish. I believe the very small particles are oxidized to form $CO_2$. When the same experiment is conducted in an argon atmosphere the particle continues to break into even smaller parts until they are border line invisible to the unaided eye (i.e. about 0.1 to 0.05 micron).

The above discoveries have lead to important improvements in my laser hair removal process.

Footprint Defined

I have discovered that instead of cleaning the carbon-oil suspension off the surface of the skin prior to the laser illumination; a better result can be obtained by leaving a thin film of the carbon-oil suspension on the surface. The first one or two pulses will cause essentially all of the particles on the surface to break apart violently leaving a clean spot on the skin surface exactly defining the footprint of the laser beam. Therefore there is no doubt which area of the skin has been treated.

Figure 2A:
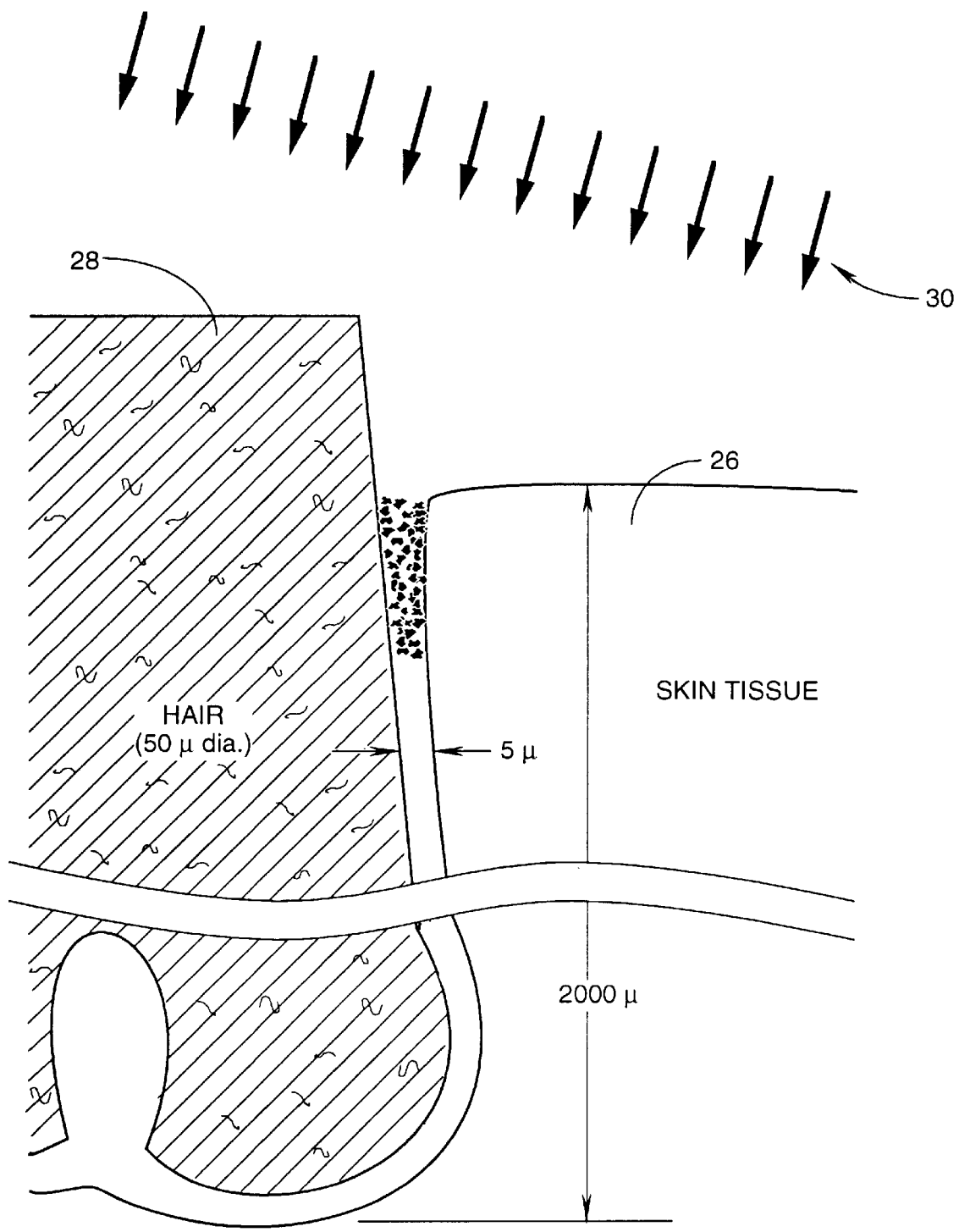
FIGS. 2A through 2E shows the graphite particles at various stages of fragmentation during a preferred process of hair removal.

Scattering Particles Fill Duct (In air the effect of the beam illuminating a thin film of our carbon-oil mixture is that the particles are scattered widely, some to distances of more than one meter through he air.) A more important effect of the violent breaking apart of the small carbon particle is that many of the scattered fragments will penetrate deeply into the hair duct during the first 3 or 4 pulses as a result of the large amount of kinetic energy imparted to the fragments. Also the force of these tiny explosions imparts kinetic energy to unfractured particles. During subsequent pulses these fragments will be absorbing energy from the pulse at locations deep within the duct. The effect is shown graphically in FIGS. 2A through 2E and is discussed in the subsequent section entitled "Hair Removal Procedure." FIG. 2A represents 1 micron size particles before the first pulse. Note the size of particles shown in FIG. 2A compared to the hair which has a diameter of roughly 50 microns and extends under the surface of the skin for about 2 mm (or 2000 microns).

The space between the surface of the hair and the duct wall is a few microns (for example about 5 to 20 microns) wide and is normally filled with an oily film.

Hair in Egg White Experiment

Figure 3A:
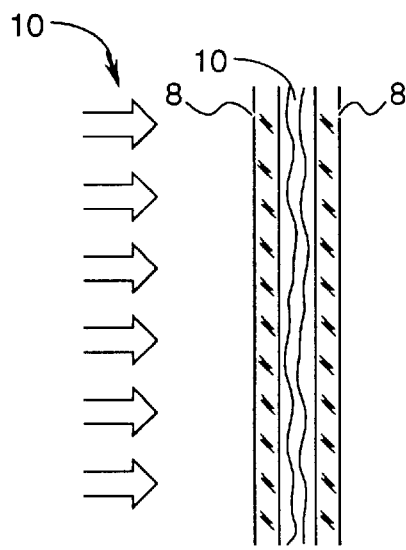
FIGS. 3A through 3C shows an experiment with turkey skin, egg white, a partially contaminant hair and a laser beam to demonstrate some of the elements of the present invention.
Figure 3A:
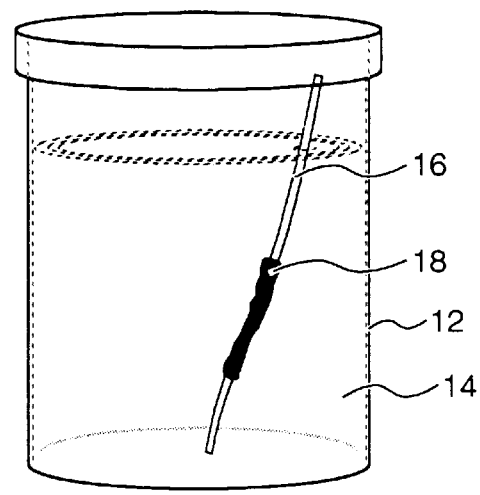
Figure 3B:
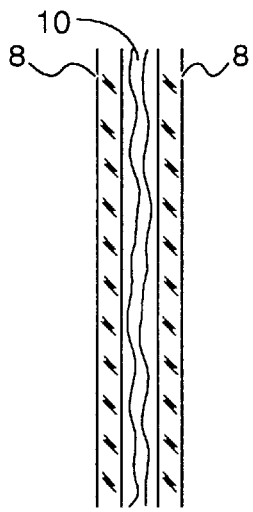
Figure 3B:
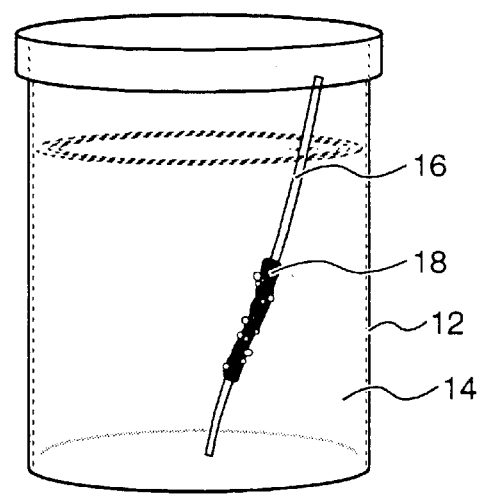
Figure 3C:
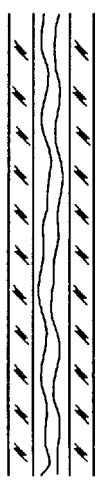
Figure 3C:
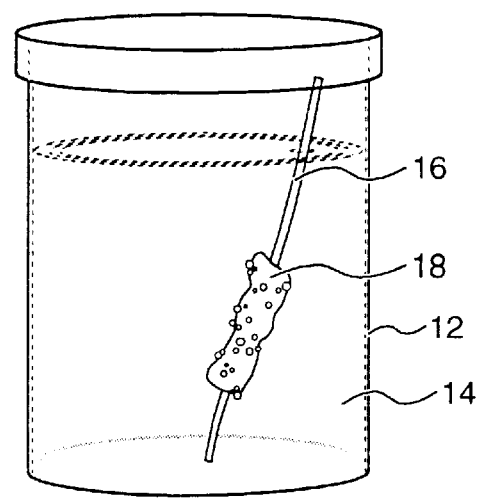

FIGS. 3A, 3B and 3C describe an experiment I performed in order to demonstrate elements of my improved hair removal process. Three layers of turkey drumsticks skin 10 was sandwiched between two glass microscopic slides. The thickness of the 3 layers of turkey skin was about 2 millimeters (approximate depth of the bottom of human hairs). A single human hair 16 (one of my own) about 10 cm long was coated over a 3 cm section with a mixture 18 of 1 micron particles of carbon and mineral oil (about equal mass). The hair was immersed in chicken egg white 14 contained in a small (5 cm diameter) vial 12. The drawing is roughly to scale except the diameter of the hair and the carbon-oil contaminant is exaggerated.

The hair including the coated section was illuminated with 100 pulses of laser radiation from a Nd:YAG laser.

The following is a description of the pulsed laser beam:

| Wavelength | 1.06 micron |
|---|---|
| Energy per pulse | 1.5 Joules |
| Beam area | ½ cm$^2$ |
| Energy density | 3 J/cm$^2$ |
| Frequency | 10 pulses per second |

Each pulse beam 20 passed through the slides and chicken skin with no apparent effect. The beacon also passed through the wall of the vial and through the egg white.

The beam was scanned over the hair so that each portion of the hair received about 5 pulses. The beam had no effect on the hair or the egg white except near the section of the hair which was coated. In that section, the carbon in the mixture absorbed sufficient energy from the beam to cook the egg white immediately surrounding the coated section of the hair. In this experiment we could watch the cooking process because uncooked egg is transparent.

FIG. 3B shows the result of the first 10 pulses of beam 20 (about 3 pulses into the carbon) passing through the elements of this experiment. The only discernible effect of these pulses was an obvious heating and cooking of the egg white immediately adjacent to the coated section of the hair. Some fragments of the particle were thrown off the hair but were trapped in the immediate surrounding egg white. These fragments were further fragmented by subsequent pulses into very small fragments or oxidized. FIG. 3C shows the results of the 100 pulses. The egg white tissue in the immediate vicinity of the coated section was cooked to a thickness of about 500 micron. There was no damage discernible in either the turkey skin or anywhere else in the egg white or to the hair itself other than the coated section. These conclusions apparent to the unaided eye were checked and confirmed under a microscope. Only a very few small particles of carbon remained.

Hair Removal Process

My improved hair removal process is presently undergoing clinical trials in two medical clinics, one in California and one in New Jersey. The primary purpose of these trials is to test the safety and effectiveness of the process for removal of unwanted facial hairs, usually on the chin or upper lip area.

Carbon Mixture

In the process we use a mixture of one micron medical grade carbon (graphite) particles and mineral oil. The ratio is about 1 to 1 per weight.

Application of Mixture

The hair in the to-be-treated is cut with a barber clipper to about a length of about 5 mm from the skin surface. The mixture is applied to the area to be treated. The mixture is massaged into the skin with a cotton swab until the hair ducts in the to-be-treated area are infiltrated to an estimated depth of about 20 microns. This stage of the process is depicted in FIG. 2A. In addition to the mixture infiltrated in the hair ducts, a thin film of the carbon-oil mixture (for example, about 100 particles per cm$^2$) is left on the surface of the skin in the area to be treated.

Laser Illumination

The area to be treated is then illuminated with a pulsed laser beam from a Nd:YAG laser. The beam specifications are as follows:

| Wavelength | 1.06 micron |
|---|---|
| Energy per pulse | 1.5 Joules |
| Beam area | ½ cm$^2$ |
| Energy density | 3 J/cm$^2$ |
| Frequency | 10 pulses per second |

Figure 2B:
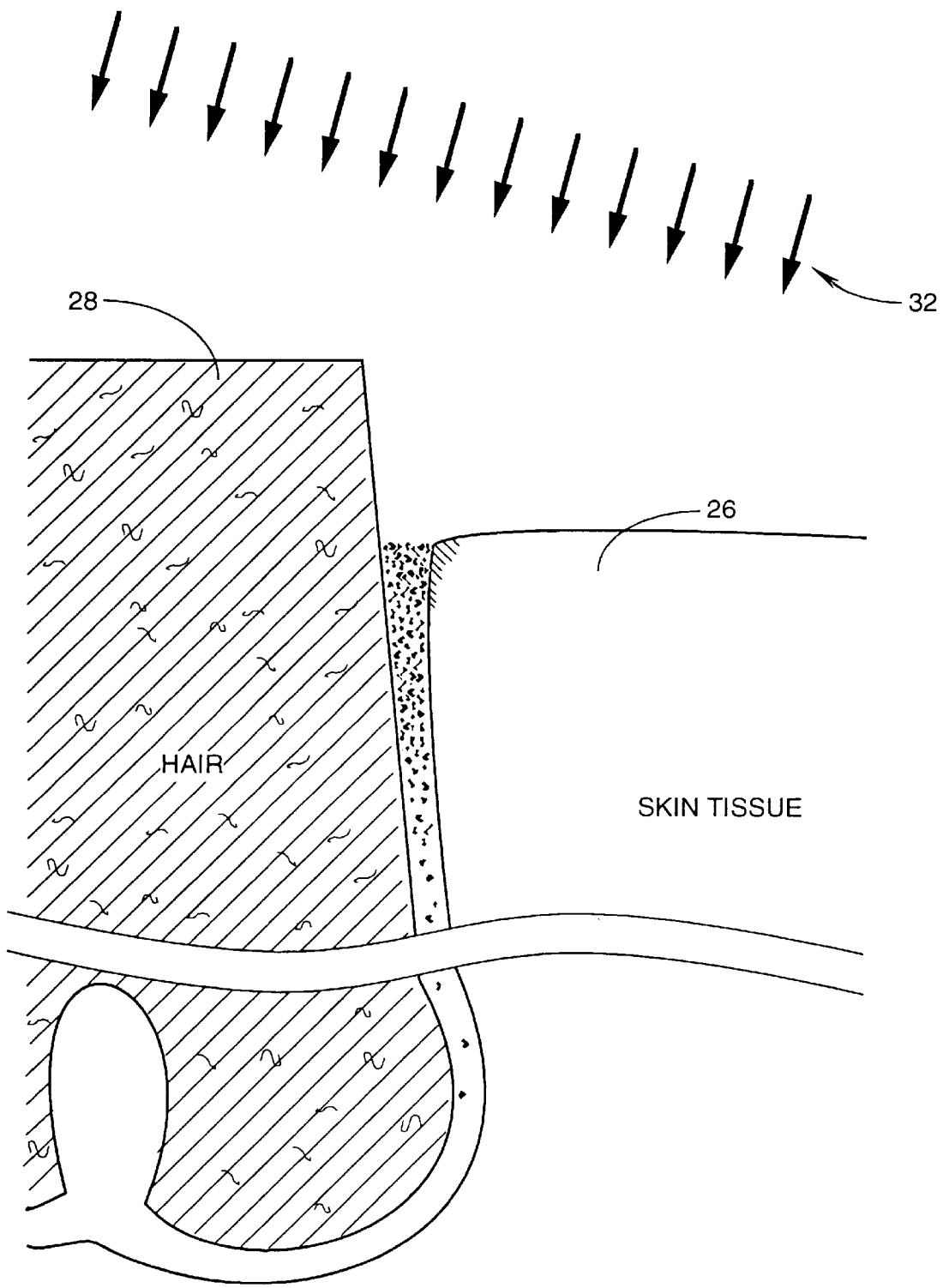
Figure 2C:
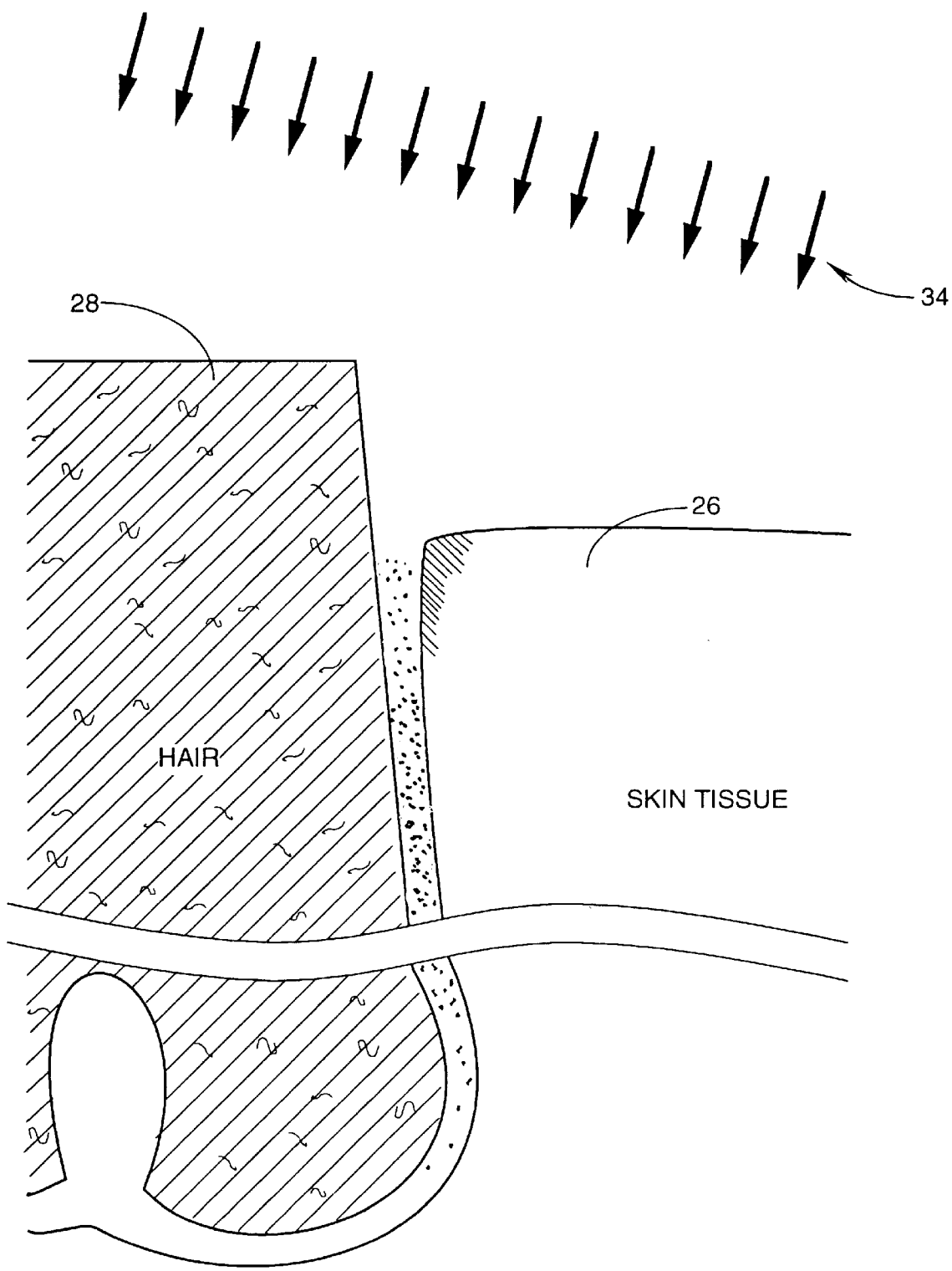
Figure 2D:
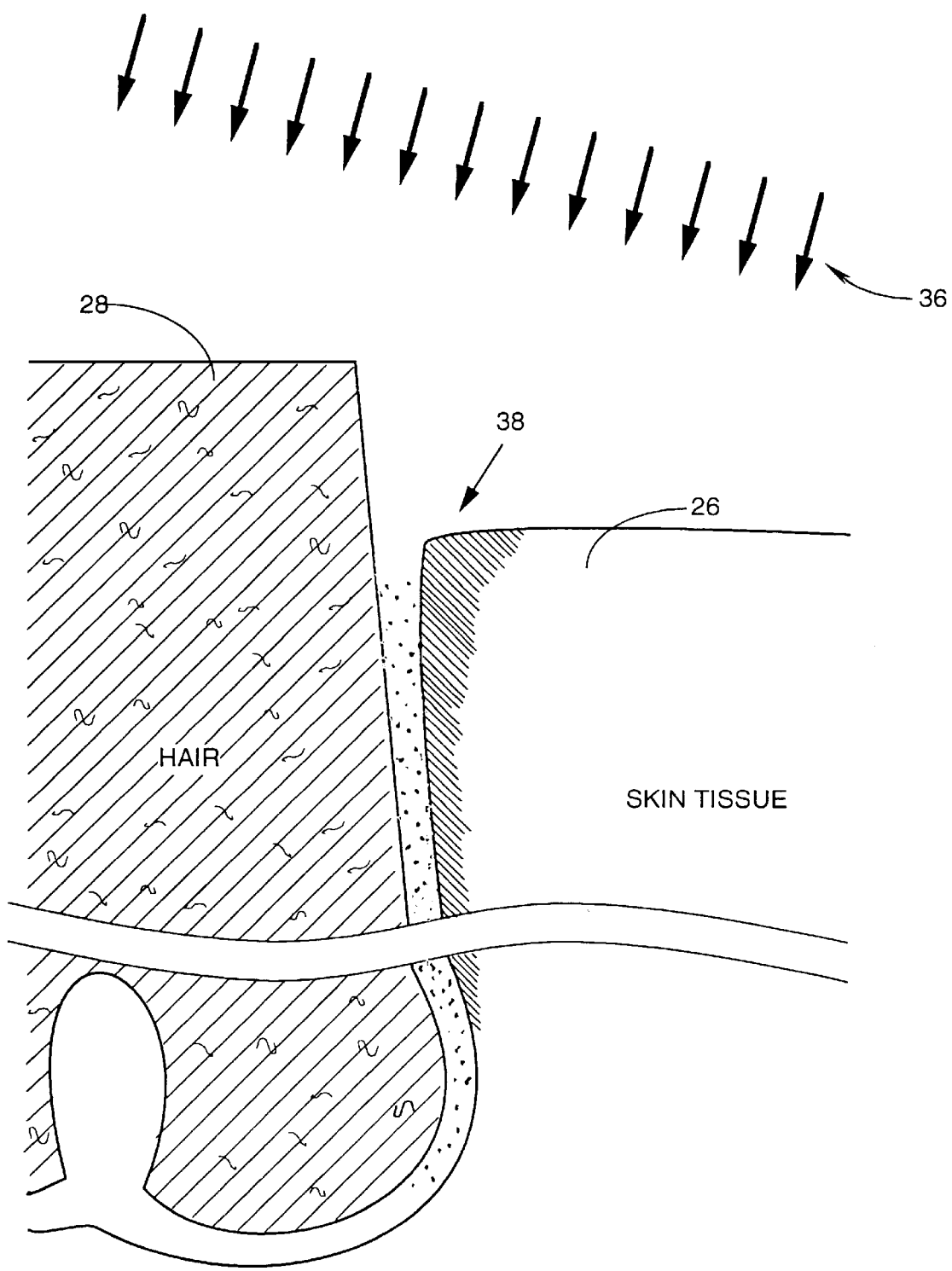
Figure 2E:
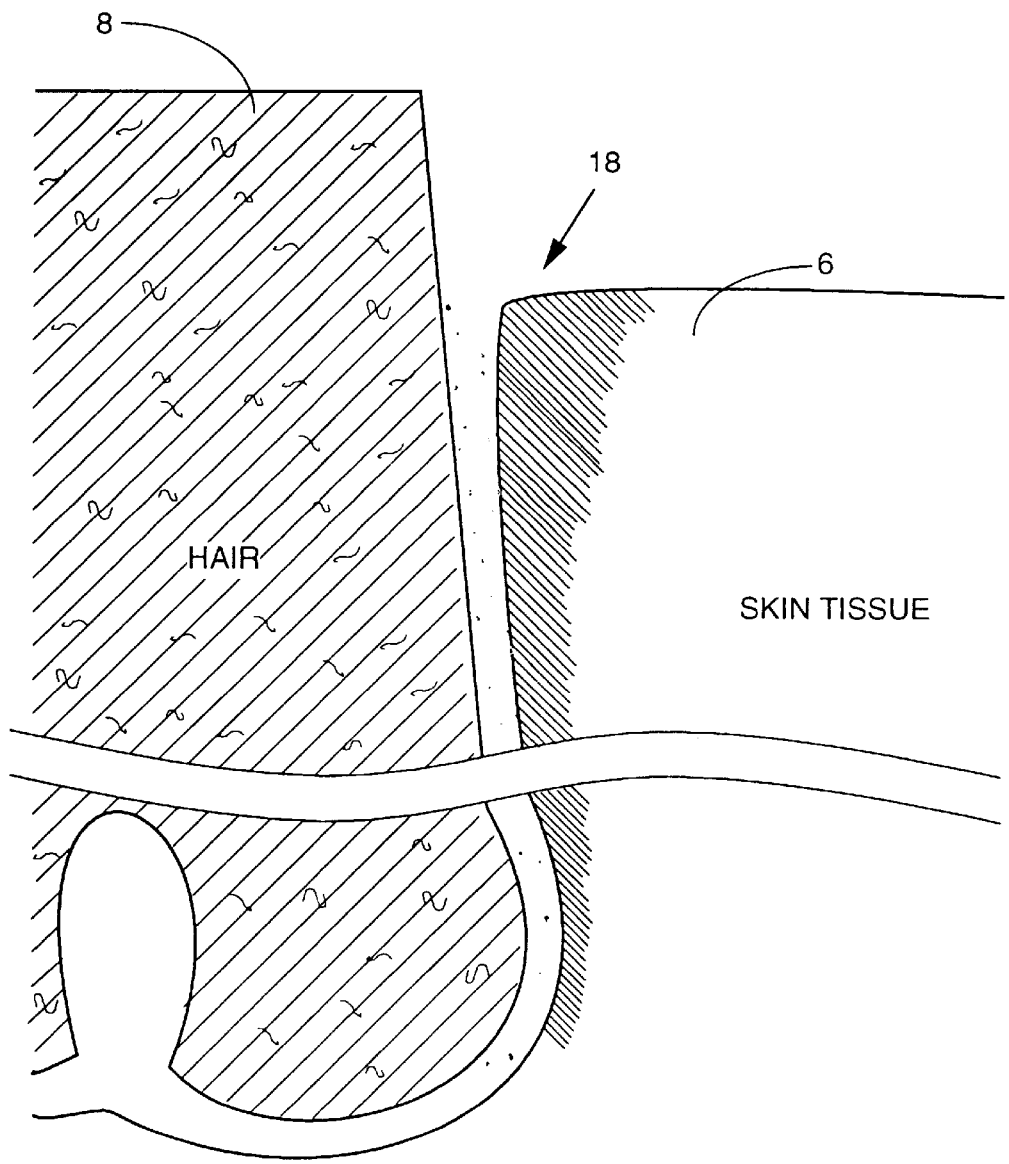

The beam is scanned over the area to be treated with each section of the skin in the area receiving about 5 pulses. The first or second pulses clean the mixture from the skin surface by violently fracturing the carbon particles so that the doctor is certain which area has been treated. As shown in FIG. 2A, the initial application of the carbon-oil mixture 25 results in carbon particles being deposited about 20 microns deep in the duct. FIG. 2B represents the results of the first pulse 30 is shown in FIG. 2A. A shockwave in the mixture spreads out the mixture for several microns. More important, the violent fragmentation of the particles sends fragments through the duct. Additional pulses further fragment the particles and distribute the fragments further down the duct. (FIG. 2C shows qualitatively the distribution of particles after about 2 pulses.) However, with each fragmentation, the particles get smaller (FIGS. 2D and 2E) and after about 4 or 5 pulses 30 through 36 the fragments have essentially disappeared. Essentially all of the energy absorbed by the particles and fragments is transferred to the skin tissue surrounding the hair. The net result is depicted in FIG. 2E. This energy is sufficient to devitalize the tissue feeding the hair so the hair dies. In FIGS. 2A through 2E arrow 38 locates the section of skin tissue damaged. Our biopsy tests indicate the thickness of the damages sections range from zero to about 20 microns. The damage to the tissue appears to be the combined result of both the heating effect of the hot carbon particles and oil and some mechanical damage due to the kinetic energy of the particles and fragments.

Results

We have had excellent results with our human tests. In an early experiment with this improved process on my own leg essentially all hair was removed and after 18 months there has been no significant regrowth. Our clinical trials with facial hair have been on-going for 13 weeks. We have been very conservative in the application of the laser beam, but the results are very good. No significant short term injury to the skin has been observed (only minor redness and in a very few cases some very minor bleeding). No long term injury has been observed. Hair removal success ratio in the treated area has ranged from about 0% to about 90% with the average being about 60%.

While the above description contains many specifics embodiments, the reader should not construe these as limitations on the scope of the invention, but merely as exemplifications of preferred embodiments thereof. For example many other small particles other than particles of graphite fragment when illuminated with these very short laser pulses. For example, small iron particles seem to behave similar to the carbon particles. Many liquids other than mineral oil could be used to help infiltrate the particles into the hair ducts. Many other oils work very well and other liquids even water could be used but the results with water are not nearly as good as with the oils. We have explored the various methods of cooling the skin prior to and during the process to reduce the minor heating effect of the skin. The laser can be applied at many different angles as measured from the angle of the hair duct. Those skilled in the art will envision many other possible variations that are within its scope. Accordingly the reader is requested to determine the scope of the invention by the appended claims and their legal equivalents, and not by the examples that have been given.

I claim:

1. A process for inhibiting growth of a plurality of hairs growing in hair ducts on a section of human skin, comprising the steps of:
   (a) applying to said skin section a contaminant comprising particles having a high absorption at at least one frequency band of light, so as to infiltrate at least a portion of said contaminant into said hair ducts,
   (b) illuminating a region of said skin section with a plurality of pulses of light, including a first pulse, at said at least one frequency band with sufficient energy to spread said contaminant deeper within said hair ducts, said energy being transferred to and from said particles and causing damage to skin tissue surrounding said hair ducts so as to inhibit growth of the hairs growing in said ducts.

2. A process as in claim 1 wherein said first pulse of light provides sufficient energy to explode at least some of said particles into two or more fragments to spread said contaminant in said hair ducts.

3. A process as in claim 2 wherein said pulses of light subsequent to said first pulse provide sufficient energy to explode at least some of said fragments into additional fragments to further spread said contaminant within said hair ducts.

4. A process as in claim 1 further comprising the step of:
   (c) cooling said skin section prior to and during said illuminating to reduce heating of the skin.

5. A process as in claim 1 wherein said illuminating is repeated until said damage to skin tissue surrounding said hair ducts destroys tissue nourishing the hairs growing in said hair ducts.

6. A process as in claim 5 wherein said illumination steps are repeated until substantially all the fragments are smaller than 0.05 microns.

7. A process as in claim 1 wherein said particles comprise graphite particles.

8. A process as in claim 1 wherein said pulses define a pulse duration measured at one half maximum power of the pulses and said pulse duration is no longer than about 30 nanoseconds.

9. A process as in claim 1 wherein said pulses of light are provided by a Nd:YAG laser operating at a wavelength of about 1.06 microns.

10. A process as in claim 9 wherein a portion of said particles are small enough to penetrate said hair ducts and larger than about 1.0 micron.

11. The process as in claim 9 wherein the laser has a beam with an energy density of about 3 J/cm$^2$.

12. The process as in claim 9 wherein the laser provides pulses of the light having a duration at about one-half maximum power of about 10 nanoseconds and a peak power of about 150 megawatts.

13. The process as in claim 2 or 9 wherein the pulses of light produce a beam with a cross-sectional area of about 0.5 cm$^2$.

14. The process as in claim 13 wherein said beam is scanned over portions of said section of skin so as to deliver about 5 pulses of the beam to each portion.

15. The process as in claim 2 or 9 wherein the frequency of the pulses is about 10 Hz.

16. The process as in claim 7 or 9 wherein the energy transferred to said contaminant heats the contaminant to a temperature of from about 70° C. to about 80° C.

17. A process as in claim 1 wherein a portion of said particles are small enough to penetrate said hair ducts and larger than about 0.5 micron.

18. A process as in claim 1 wherein said illumination step is repeated until substantially all of the particles have been exploded and fragments of the particles have been exploded and fragments of the particles have been exploded to produce smaller fragments until substantially all of the fragments remaining in the hair ducts are smaller than about 0.1 micron.

19. A process as in claim 18 wherein said illuminating is continued until substantially all the fragments are smaller than about 0.05 microns.

20. A process as in claim 1 wherein applying said contaminant includes leaving a thin film of said contaminant on said skin section prior to said illuminating, said illuminating including exploding a substantial number of the particles in said thin film with said first pulse so as to define a footprint of said first pulse.

21. A process as in claim 1 or 9 wherein said contaminant comprises graphite particles mixed with an oil.

22. A process as in claim 21, wherein said graphite particles and oil have a weight ratio of approximately 1:1.

23. A process as in claim 21, wherein said oil comprises mineral oil.

24. The process as in claim 1 wherein the contaminant comprises carbon particles.

25. The process as in claim 1 wherein the contaminant comprises iron particles.

26. The process as in claim 1 wherein the damage to skin tissue surrounding said hair ducts inhibits nourishment of said hairs.

* * * * *